(12) United States Patent  
Holley

(10) Patent No.: US 6,873,719 B1  
(45) Date of Patent: Mar. 29, 2005

(54) IMAGE ACQUISITION APPARATUS

(75) Inventor: John Ernest Foster Holley, N. Westerham (GB)

(73) Assignee: Oxoid Limited, Basingstoke (GB)

( * ) Notice: Subject to any disclaimer, the term of this patent is extended or adjusted under 35 U.S.C. 154(b) by 0 days.

(21) Appl. No.: 09/762,913

(22) PCT Filed: Aug. 11, 1999

(86) PCT No.: PCT/GB99/02645

§ 371 (c)(1),
(2), (4) Date: Apr. 16, 2001

(87) PCT Pub. No.: WO00/11593

PCT Pub. Date: Mar. 2, 2000

(30) Foreign Application Priority Data

Aug. 19, 1998 (GB) .............................................. 9817982  
Dec. 24, 1998 (GB) .............................................. 9828668

(51) Int. Cl.$^7$ ................................................ G06K 9/00
(52) U.S. Cl. ........................ 382/133; 382/141; 435/7.7; 348/127; 356/39
(58) Field of Search ............................... 382/128, 129, 382/130, 131, 132, 133, 134; 210/787; 435/7.2, 7.23, 7.24, 7.25, 7.4, 7.7, 7.91, 288.7, 287.4, 287.1; 356/426, 427, 428, 39, 44, 507; 250/559.11; 209/524

(56) References Cited

U.S. PATENT DOCUMENTS

| 4,956,103 | A | * | 9/1990 | Jessop et al. ............... 210/787 |
| 5,485,527 | A | * | 1/1996 | Bacus et al. ................ 382/128 |
| 5,556,764 | A | * | 9/1996 | Sizto et al. ................ 435/7.24 |
| 5,618,729 | A | * | 4/1997 | Izraelevitz et al. ...... 435/288.7 |
| 5,740,270 | A | * | 4/1998 | Rutenberg et al. .......... 382/133 |
| 5,911,000 | A | * | 6/1999 | Shen ........................... 382/134 |
| 5,970,163 | A | * | 10/1999 | Iwasaki et al. ............. 382/128 |

* cited by examiner

Primary Examiner—Bhavesh M. Mehta  
Assistant Examiner—Seyed Azarian  
(74) Attorney, Agent, or Firm—Rader, Fishman & Grauer PLLC

(57) ABSTRACT

Image acquisition apparatus is used to obtain images of contents of containers for use in, for example, antibiotic susceptibility testing. The apparatus has image capture means, such as a scanner (6) for obtaining images of the contents of the containers which are supported on receiving means (1) for receiving the containers and positioning them within the field of view of the scanner (6). In addition, light deflecting means, such as reflectors, are provided for deflecting light from identification markings on the sides of the containers into the scanner (6) to enable the latter also to obtain an image of said markings, and thus to enable the apparatus to identify each container.

14 Claims, 2 Drawing Sheets

IMAGE ACQUISITION APPARATUS

FIELD OF THE INVENTION

This invention relates to apparatus for acquiring an image of the contents of a container for subsequent analysis. The apparatus is especially, but not exclusively, applicable to systems for use in antibiotic susceptibility testing of micro-organisms.

BACKGROUND OF THE INVENTION

Antibiotic susceptibility testing has for many years been used as a means for identifying particular groups or species of micro-organisms, or for identifying an antibiotic type or dose level most appropriate for dealing with a particular clinical infection.

Usually, six or eight discs, carrying different types of antibiotic or the same type of antibiotic but in different concentrations, are placed in a circular array on a petri dish. The dish contains a layer of growth medium, such as agar gel, to which a material containing a micro-organism to be analysed is applied.

The antibiotic diffuses out of each disc into the surrounding growth medium and establishes a radial concentration gradient around the disc. The diameter of the zone of inhibited micro-organism growth around the disc is indicative of the relative susceptibility of the micro-organisms to the antibiotic on that disc. The detailed morphology of the zone can also provide information on the species or genus of micro-organism presence.

There have been various proposals for automating the analysis of the contents of the petri dishes, especially the inhibition zones, involving the use of an overhead video camera connected to a data processing device.

The petri dishes used in such tests are commonly provided with identification markings. For example, in hospitals, the patient from whom the micro-organism in a petri dish has been extracted is identified by means of a bar code applied to the side of the petri dish.

Since the sides of the petri dishes are vertical, it is difficult if not impossible for the bar codes to be read by an overhead camera of an automatic analysis system.

SUMMARY OF THE INVENTION

According to a first aspect of the invention, there is provided image acquisition apparatus for acquiring an image of the contents of a container, carrying identification markings, the apparatus comprising image capture means for obtaining an image of the contents of the container, receiving means for receiving the container and positioning it within the field of view of the image capture means, the apparatus further comprising light deflecting means for deflecting light from said identification markings to the image capture means to enable the latter also to obtain an image of said markings.

Thus, the deflection means enables the apparatus to acquire an image not only of the contents of the container, but also of the identification markings. If the apparatus is used in an AST system, a signal representative of that image can be supplied to a data processor which analyses the contents of the container (for example a petri dish) to determine the size and shape of the zones of inhibition around the carrier discs, and also to read the identification markings.

Preferably, the light deflecting means comprises a reflecting means positioned, on the receiving means, adjacent a location at which a container is to be received.

Conveniently, the image capture means is adapted to face downwards so as to obtain an image of the contents of a container situated under the image capture means. In this case, the reflecting means is preferably so inclined, relative to the receiving means, as to reflect light which is incident thereon from a horizontal direction upwards into the image capture means.

Thus, if the apparatus is to be used with petri dishes having identification markings on their vertical sides, the reflecting means may be inclined at an angle of 45°, but is preferably inclined at an angle of 30° to the horizontal or (alternatively) at 30° to the vertical.

Preferably, the reflecting means is annular.

This enables the reflecting means to surround a container, such as a petri dish, so that the image of identification markings on the container wall can be reflected into the image capture means regardless of the orientation of the container.

Preferably, the receiving means comprises a support having a well recess or depression for receiving and accommodating said container, wherein said reflecting means is incorporated into the wall of the well.

Preferably, the well wall is frusto-conical, thereby to provide said inclination of the reflecting means, and the support may to advantage be formed of metal, at least part of the wall of the well having been polished to provide said reflecting means.

Preferably, the well is one of a plurality of such wells in the support, each for accommodating a respective container.

The image capture means conveniently comprises a scanner.

The invention also lies in apparatus as herein above described, and a plurality of containers, such as petri dishes, each carrying identification markings.

Preferably, the output of the image capture means is connected to data processing means for identifying a container on the receiving means and analysing the image of the container contents.

Preferably, the apparatus is adapted to perform antibiotic susceptibility tests to identify a particular micro-organism grown on a culture in a container.

BRIEF DESCRIPTION OF THE DRAWINGS

The invention will now be described, by way of example only, with reference to the accompanying drawings in which.

DETAILED DESCRIPTION

Figure 1:
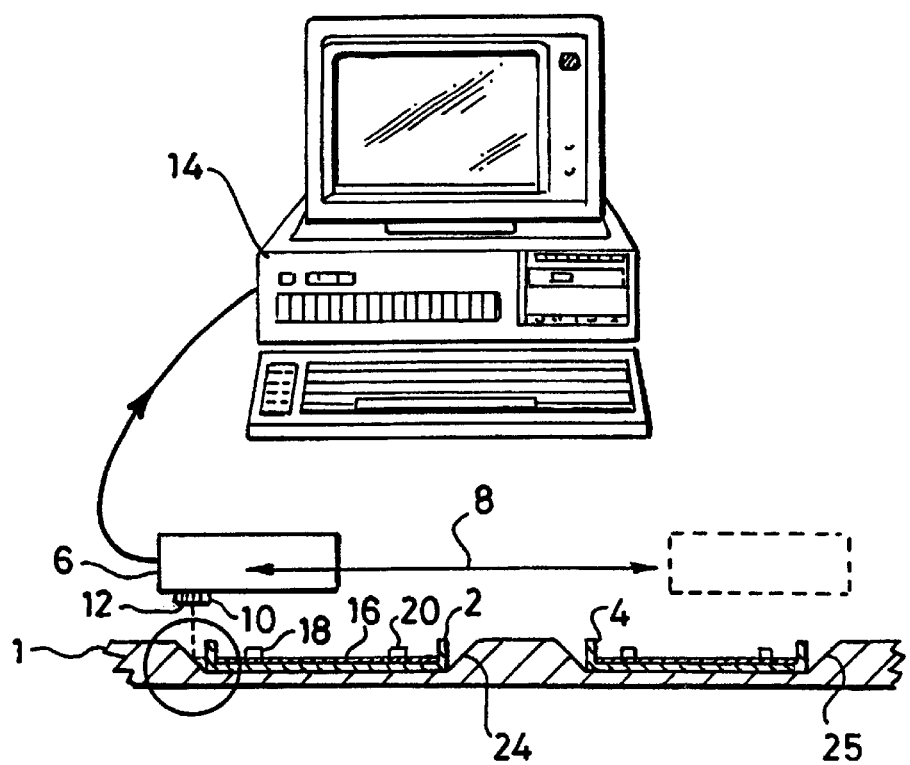
FIG. 1 is a schematic view of apparatus in accordance with the invention.

With reference to FIG. 1, an embodiment of apparatus in accordance with the invention comprises a metal carrier plate 1 which acts as support means for a number of petri dishes, for example 2 and 4. The plate 1 is situated underneath an image scanner which is of the same type as a conventional flat bed scanner, and includes a scanning head 6. For the sake of clarity, only the scanning head 6 of the scanner is shown in FIG. 1. The head 6 is mounted in the scanner via a suitable drive for causing the head to sweep over the whole plate 1 in the directions indicated by the arrow 8. The head 6 includes an output 10 which directs a beam of light vertically downwards onto the support 1, and hence the petri dishes. Light reflected from the support 1 and petri dishes is received at an input 12 for focusing onto a light sensitive receptor in the head 6 for converting the received light into an electrical signal representative of the image of the plate and dishes thereon captured by the scanning head 6.

That signal is fed to a computer 14, which is arranged to convert the signal into a digital data stream, and to manipulate and analyse the image represented thereby. The apparatus is intended for use in AST analysis of micro-organisms grown on an agar gel layer such as a layer 16 in the dish 2. The growth is affected by antibiotics initially carried by carrier discs, two of which are shown at 18 and 20 on the layer 16. There are various ways in which the analysis of the image of the areas of growth (or inhibition of growth) can be performed by the computer 14 (but these are not the subject of the present invention)

The computer may, for example, measure the area of the zone of inhibited growth of micro-organisms around the disc and, in some cases, may be operable to send character codes on the discs (possibly with the aid or orientation markings also on the discs) to identify the type and/or concentration of reagent (eg an antibiotic) carried by the disc.

However, a description of how a computer of an AST testing apparatus can analyse acquired images is provided in the present Applicants' PCT Patent Application published under No. WO99/02645. The relevant subject matter of WO99/02645 is accordingly incorporated into this specification by reference.

Figure 4:
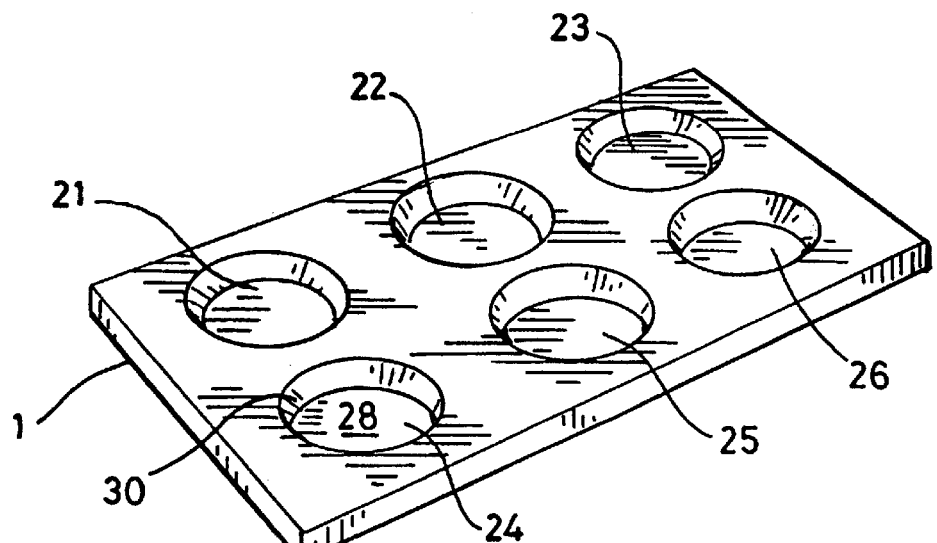
FIG. 4 is a perspective view of the support.

With reference to FIG. 4, the upper surface of the plate 1 is provided with six circular wells recesses or depressions 21–26, each for accommodating a respective petri dish. The wells are arranged in two rows of three. Since the wells are identical, only the well 24 will be described. This well has a circular base 28 from which a frusto-conical wall 30 rises. The wall 30 flares from the bottom to the top of the well 24, and is polished so as to define an annular reflecting surface which in this embodiment makes an angle of approximately 45° with the base 28.

In another embodiment of the invention, the reflecting means is inclined at an angle of 30° to the vertical. In a further embodiment, the reflecting means is inclined at an angle of 30° to the horizontal.

Figure 2:
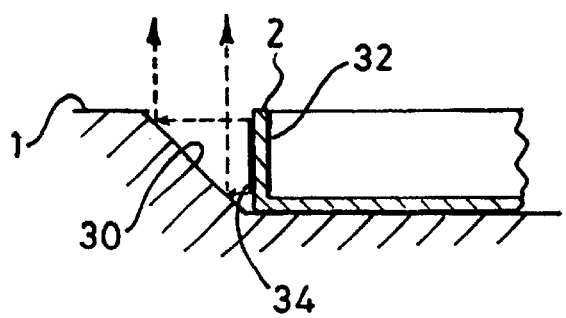
FIG. 2 is a more detailed sectional side elevation of part of the apparatus shown in FIG. 1.
Figure 3:
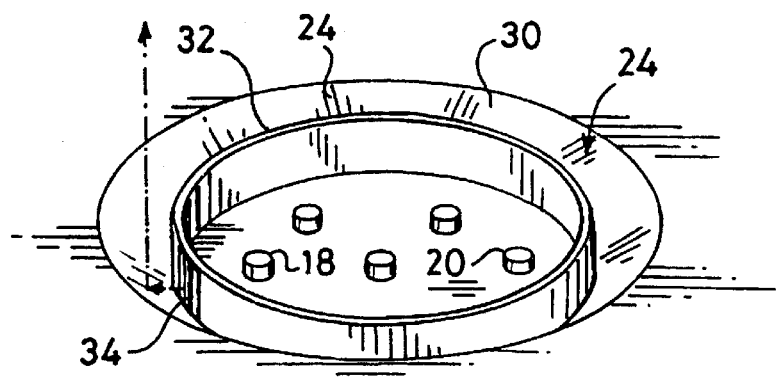
FIG. 3 is a perspective view of a petri dish and part of a support for the apparatus.

As can be seen from FIGS. 1–3, the well 24 accommodates the petri dish 2 which, like the other petri dishes, has a vertical, cylindrical side wall 32, the exterior of which carries identification markings in the form of a bar code 34 (FIGS. 2 and 3) printed on a self adhesive label stuck to the wall 32.

Figure 5:
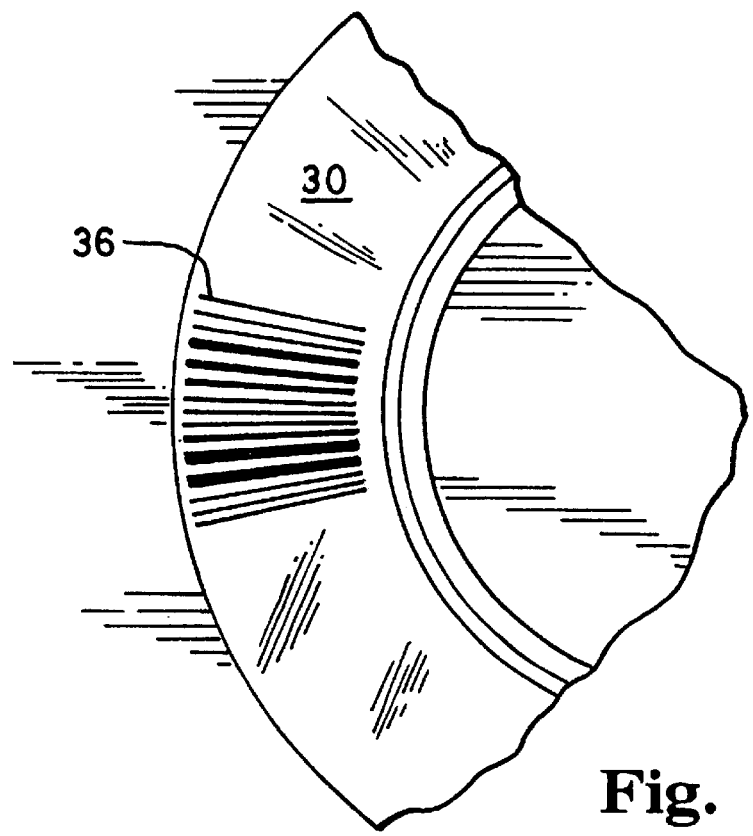
FIG. 5 is a plan view of part of the support with a petri dish therein.

The scanner head is not able to obtain images of the vertical side wall of the petri dish 2, and therefore cannot directly read the bar code 34 from the latter. However, the image of the bar code 34 is reflected from the wall 30 as shown by the broken lines in FIGS. 2 and 3. Accordingly, the scanning head 6 can form an image of the reflection of the bar code 34 in the wall 30 as shown in FIG. 5, in which the reflected image of the bar code 34 is denoted by the reference numeral 36.

The image 36 is laterally inverted by virtue of its reflection in the surface 30. However, this can be handled by the image processing software in the computer 14 which can reverse the direction of reading of the bar code 34. Alternatively, the bar code itself can be laterally inverted compared with the norm so that it can be read by the computer 14 as if it were a conventionally orientated bar code.

What is claimed is:

1. Image acquisition for acquiring an image of the contents of a container, a side of the container carrying identification markings, the apparatus comprising overhead image capture means for obtaining an image of the contents of a container situated under the image capture means, receiving means for receiving the container and positioning it within the field of view of the image capture means, the apparatus further comprising light deflecting means for deflecting light from said identification markings to the image capture means to enable the latter also to obtain an image of said markings.

2. Apparatus according to claim 1, in which the light deflecting means comprises a reflecting means positioned, on the receiving means, adjacent a location at which a container is to be received.

3. Apparatus according to claim 2, in which the reflecting means is so inclined, relative to the receiving means, as to reflect light which is incident thereon from a horizontal direction upwards into the image capture means.

4. Apparatus according to claim 3, in which the reflecting means is inclined at an angle of 45° to enable the scanning means to read identification markings on the vertical sides of containers for use therewith.

5. Apparatus according to claim 3, in which the reflecting means is inclined at an angle of 30° to the horizontal or 30° to the vertical, to enable the apparatus to read the markings on the vertical sides of containers for use therewith.

6. Apparatus according to claim 2 in which the reflecting means is annular, the arrangement being such that, in use, the reflecting means surrounds a container in the receiving means of the apparatus.

7. Apparatus according to claim 2, in which the receiving means comprises a support having a well, recess or depression for receiving and accommodating said container, wherein said reflecting means is incorporated into the wall of the well.

8. Apparatus according to claim 7, in which the well wall is frusto-conical, thereby to provide said inclination of the reflecting means.

9. Apparatus according to claim 7, in which the support is formed of metal, at least part of the wall of the well having a smooth surface to provide said reflecting means.

10. Apparatus according to claim 7, in which the well is one of a plurality of such wells in the support, each for accommodating a respective container.

11. Apparatus according to claim 1, in which image capture means comprises a scanner.

12. Analysis apparatus comprising image acquisition apparatus according to claim 1 and a plurality of containers, comprising petri dishes, each carrying respective identification markings.

13. Analysis apparatus according to claim 12, in which the output of the image capture means is connected to data processing means for identifying a container on the receiving means and analysing the image of the container contents.

14. Analysis apparatus according to claim 12, in which the apparatus is so arranged to be operable to perform antibiotic susceptibility tests to identify a particular micro-organism grown on a culture in a container.

* * * * *